(12) United States Patent
Cohen et al.

(10) Patent No.: US 12,708,697 B2
(45) Date of Patent: Aug. 18, 2026

(54) TISSUE AND ORGAN REPLACEMENTS AND METHODS OF MAKING THEREOF

(71) Applicant: TDBT IP Inc., Long Island City, NY (US)

(72) Inventors: Daniel Cohen, Brooklyn, NY (US); Scott Douglas Cornez, New York, NY (US); Jerson Mezquita, Bronx, NY (US); Nathaniel Bachrach, Clifton, NJ (US)

(73) Assignee: TDBT IP Inc., New York, NY (US)

( * ) Notice: Subject to any disclaimer, the term of this patent is extended or adjusted under 35 U.S.C. 154(b) by 0 days.

(21) Appl. No.: 17/487,723

(22) Filed: Sep. 28, 2021

(65) Prior Publication Data

US 2022/0016314 A1 Jan. 20, 2022

Related U.S. Application Data

(63) Continuation of application No. PCT/US2020/025498, filed on Mar. 27, 2020.

(Continued)

(51) Int. Cl.

*A61L 27/26* (2006.01)
*A61F 2/00* (2006.01)

(Continued)

(52) U.S. Cl.

CPC ............ *A61L 27/26* (2013.01); *A61F 2/0059* (2013.01); *A61F 2/50* (2013.01); *A61F 2/5044* (2013.01);

(Continued)

(58) Field of Classification Search

CPC ...... A61F 2/186; A61F 2/105; A61F 2/10059; A61F 2/18; A61F 2/12; A61F 2/24;

(Continued)

(56) References Cited

U.S. PATENT DOCUMENTS 3,257,668 A * 6/1966 Braley ..................... A61F 2/18 623/10
6,773,713 B2 8/2004 Bonassar et al.

(Continued)

FOREIGN PATENT DOCUMENTS

CN 106999635 A 8/2017
CN 107502061 A 12/2017

(Continued)

OTHER PUBLICATIONS

International Search Report and Written Opinion issued in PCT/US2020/025498, mailed Jul. 3, 2020, 13 pages.

(Continued)

*Primary Examiner* — Christie Bahena
(74) *Attorney, Agent, or Firm* — Schmeiser Olsen PLLC; Jared L. DuJack, Esq.

(57) ABSTRACT

A tissue or organ replacement includes a tissue-engineered construct that includes one or more bio ink compositions and a biocompatible support structure. The support structure includes one or more external supports, one or more internal supports, or combinations thereof of a biocompatible material. The composition has a three-dimensional (3D) shape, and the biocompatible material is present in an amount of about 1% to about 100% by weight of the biocompatible support structure.

17 Claims, 6 Drawing Sheets

Related U.S. Application Data

(60) Provisional application No. 62/826,745, filed on Mar. 29, 2019.

(51) Int. Cl.

| | |
|---|---|
| ***A61F 2/50*** | (2006.01) |
| ***A61F 11/00*** | (2022.01) |
| ***A61L 27/52*** | (2006.01) |
| ***B29C 64/106*** | (2017.01) |
| ***B29C 64/40*** | (2017.01) |
| ***B33Y 10/00*** | (2015.01) |
| ***B33Y 40/20*** | (2020.01) |
| ***B33Y 80/00*** | (2015.01) |
| *B29L 31/00* | (2006.01) |

(52) U.S. Cl.

CPC ............... *A61F 11/00* (2013.01); *A61L 27/52* (2013.01); *B29C 64/106* (2017.08); *B29C 64/40* (2017.08); *B33Y 10/00* (2014.12); *B33Y 40/20* (2020.01); *B33Y 80/00* (2014.12); *A61F 2002/5055* (2013.01); *A61L 2430/14* (2013.01); *B29L 2031/7532* (2013.01)

(58) Field of Classification Search

CPC .................. A61F 2/2846; A61F 2/3872; A61F 2002/183; A61F 2002/2835; A61F 2002/2839; A61F 2002/2875; A61F 2002/2889; A61L 2430/14; A61L 27/00; C09D 11/101; B33Y 80/00

USPC ........................................................... 623/10

See application file for complete search history.

(56) References Cited

U.S. PATENT DOCUMENTS

| | | | | |
|---|---|---|---|---|
| 9,044,335 | B2 | 6/2015 | Bonassar et al. | |
| 2007/0042491 | A1* | 2/2007 | Karp | C12N 5/0654 435/368 |
| 2016/0100934 | A1* | 4/2016 | Hickey | A61L 27/3821 424/602 |
| 2016/0303284 | A1 | 10/2016 | Borde et al. | |
| 2017/0348458 | A1 | 12/2017 | Kesti et al. | |
| 2019/0016913 | A1* | 1/2019 | Shastri | C08B 37/0039 |
| 2020/0163752 | A1* | 5/2020 | Salas | A61F 2/3094 |

FOREIGN PATENT DOCUMENTS

| | | | | |
|---|---|---|---|---|
| JP | 2018-501845 | A | 1/2018 | |
| KR | 20120088928 | | 8/2012 | |
| KR | 20170012099 | | 10/2018 | |
| WO | WO-2010084481 | A1 * | 7/2010 | A61F 2/02 |
| WO | WO-2016092106 | A1 * | 6/2016 | A61L 27/20 |
| WO | WO/2017/205695 | | 11/2017 | |
| WO | WO-2017214736 | A1 * | 12/2017 | A61L 27/54 |
| WO | WO-2018071639 | A1 * | 4/2018 | A61L 27/26 |
| WO | WO/2018/218060 | | 11/2018 | |

OTHER PUBLICATIONS

Shim et al., "Development of a hybrid scaffold with synthetic biomaterials and hydrogel using solid freeform fabrication technology," Biofabrication (2011) vol. 3, No. 2, Article 034102, 9 pages.

* cited by examiner

TISSUE AND ORGAN REPLACEMENTS AND METHODS OF MAKING THEREOF

CROSS-REFERENCE TO RELATED APPLICATIONS

This application is a continuation of International Application No. PCT/US2020/025498, filed Mar. 27, 2020, which claims the benefit of priority to U.S. Provisional Application No. 62/826,745, filed Mar. 29, 2019, the entirety of which are incorporated herein by reference.

TECHNICAL FIELD

The present technology relates generally to biological replacement tissues or organs for transplants and implants and methods of preparing the same. More particularly, the present technology relates to tissue and organ replacements having a biocompatible support structure and tissue-engineered construct and methods of fabricating thereof.

SUMMARY

In one aspect, the present technology provides a tissue or organ replacement that includes a tissue-engineered construct that includes one or more bio ink compositions and a biocompatible support structure that includes one or more external supports, internal supports, or combinations thereof of a biocompatible material, where the composition has a three-dimensional (3D) shape, and the biocompatible material is present in an amount of about 1% to about 100% by weight of the biocompatible support structure.

In a related aspect, the present technology provides a method of fabricating the tissue or organ replacement composition that includes fabricating a biocompatible support structure as described herein in any embodiment; fabricating a tissue-engineered construct as described herein in any embodiment comprising depositing one or more bio ink compositions as described herein in any embodiment in or around the biocompatible support structure; crosslinking the one or more bio ink compositions, and optionally repeating the depositing and crosslinking steps, to form the tissue-engineered construct; and curing the tissue or organ replacement composition; where the biocompatible support structure includes one or more of external supports, internal supports, or combinations thereof of a biocompatible material, and the biocompatible material is present in an amount of about 1% to about 100% by weight of the biocompatible support structure.

BRIEF DESCRIPTION OF THE DRAWINGS

As discussed below.

FIG. 4A shows a general exemplary method for fabricating the tissue or organ replacement composition according to an embodiment of the present technology.

FIG. 4B shows an exemplary process for fabricating biocompatible support structures (external supports and/or internal supports).

FIG. 4C shows an exemplary method for fabricating a tissue-engineered construct according to at least one embodiment.

FIG. 4D shows a flow diagram for an exemplary method of curing a construct according to at least one embodiment.

DETAILED DESCRIPTION

Figure 1A:
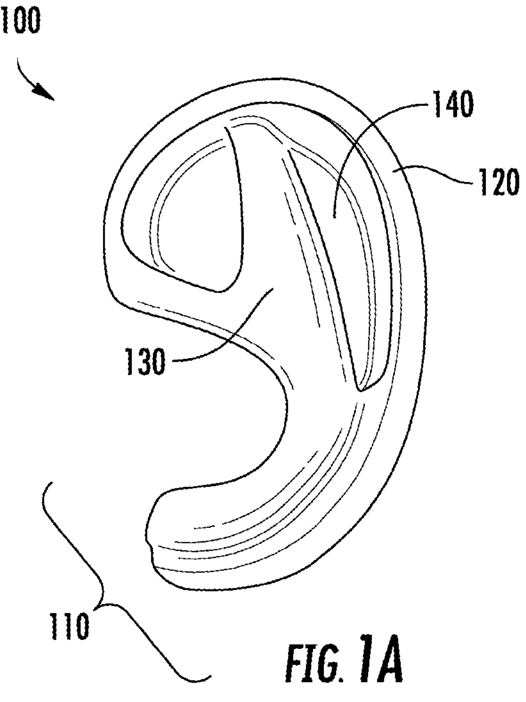
FIG. 1A provides a perspective view of a tissue/organ replacement composition according to an embodiment of the present technology that includes a biocompatible support structure, where the biocompatible support structure has an external support partially covering outer two-dimensional (2D) surfaces of the tissue-engineered construct and an internal support partially encapsulated by the tissue-engineered construct.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The term "biocompatible material" refers to a material derived from a natural or synthetic source having the ability to perform its desired function in the body of a subject without eliciting any undesirable local or systemic effects. As used herein, biocompatible materials may also refer to materials that are biodegradable, bioabsorbable, bioresorbable, or a combination of two or more thereof under physiological conditions. The term "biodegradable" refers to a material that can be broken down into basic substances through normal environmental processes and/or by the action of living things, such as, microorganisms. The term "bioabsorbable" refers to a material capable of being absorbed into living tissue. The term "bioresorbable" refers to a material that upon placement within the human body starts to dissolve (resorbed) and slowly replaced by advancing tissue. As used herein, in any embodiment, the terms "biodegradable," "bioabsorbable," and "bioresorbable" are used interchangeably.

As used herein, a "subject" or a "patient" is a mammal as described herein. The term "subject" and "patient" can be used interchangeably. As used herein, the term mammal includes, but is not limited to, a cat, dog, rodent, or primate. For example, in any embodiment herein, the mammal is a human.

The term "hydrogel" or "gel" refers to a substance formed when an organic polymer (natural or synthetic) is set or solidified to create a three-dimensional open-lattice structure that entraps molecules of water or other solution to form a gel. The solidification may occur, e.g., by aggregation, coagulation, hydrophobic interactions, or crosslinking. Hydrogels may be cellular (i.e., containing cells) or acellular (i.e., without cells). Hydrogels containing cells may rapidly solidify to keep the cells evenly suspended within a mold (or around or within another solidified gel) until the gel solidifies. Hydrogels may also be biocompatible, e.g., not toxic to cells suspended in the hydrogel.

As used herein, "2D thickness" refers to the cross-sectional thickness of the external support or internal support or an element of the support (e.g., a truss element of truss like support) from one surface to an opposing parallel surface of the supports or support elements.

As used herein, the term "collagen" refers to the main protein of connective tissue that has a high tensile strength and that has been found in most multicellular organisms. Collagen is a major fibrous protein, and it is also the non-fibrillar protein in basement membranes. It contains an abundance of glycine, proline, hydroxyproline, and hydroxylysine. Collagen is found throughout the body and is of at least 12 types (type I-XII).

Tissue/Organ Replacement of the Present Technology

In one aspect, the present technology provides a tissue or organ replacement that includes a tissue-engineered construct that includes one or more bio ink compositions and a biocompatible support structure that includes one or more external supports, internal supports, or combinations thereof of a biocompatible material, where the composition has a three-dimensional (3D) shape, and the biocompatible material is present in an amount of about 1% to about 100% by weight of the biocompatible support structure.

FIG. 1A provides a perspective view of a tissue/organ replacement composition 100 according to an embodiment of the present technology that includes a biocompatible support structure 110, where the biocompatible support structure has an external support 120 partially covering outer two-dimensional (2D) surfaces of the tissue-engineered construct 140 and an internal support 130 partially encapsulated by the tissue-engineered construct 140.

Figure 1B:
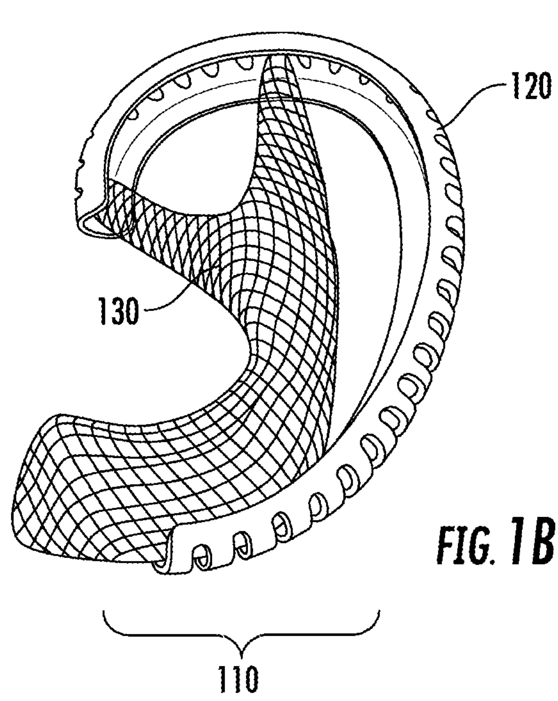
FIG. 1B provides a perspective view of the biocompatible support structure according to an embodiment of the present technology having the internal support connected to one or more 2D surfaces of the external structure.
Figure 1C:
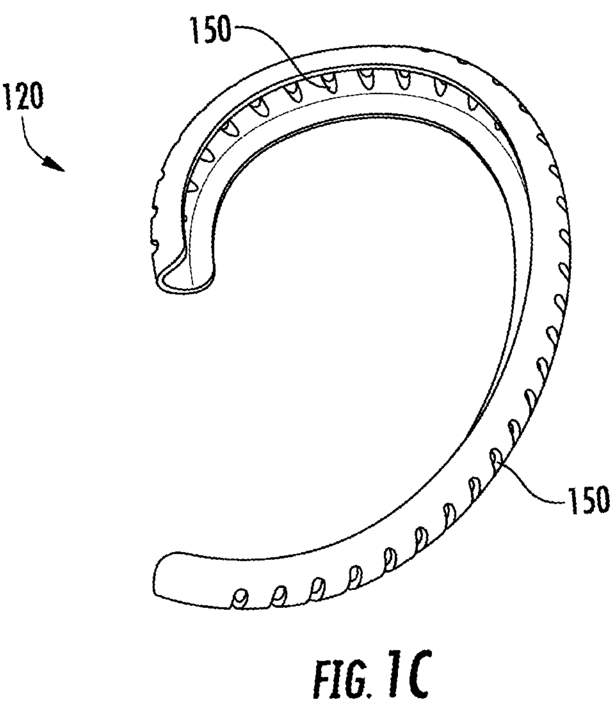
FIG. 1C provides a perspective view of the external support having one or more apertures extending there-through from one 2D surface to an opposite parallel 2D surface.
Figure 1D:
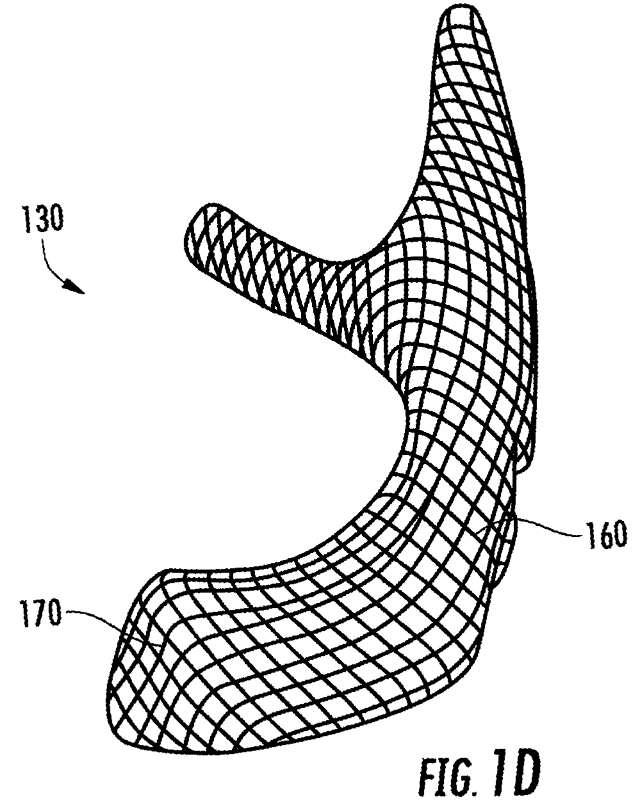
FIG. 1D provides a perspective view of an internal support according to an embodiment of the present technology having one or more apertures extending there-through from one 2D surface to an opposite parallel 2D surface of the internal support, and having a cavity.

FIG. 1B provides a perspective view of the biocompatible support structure 110 according to an embodiment of the present technology having the internal support 140 connected to one or more 2D surfaces of the external structure 120. FIG. 1C provides a perspective view of the external support 120 having one or more apertures 150 extending there-through from one 2D surface to an opposite parallel 2D surface. FIG. 1D provides a perspective view of an internal support 130 according to an embodiment of the present technology having one or more apertures 160 extending there-through from one 2D surface to an opposite parallel 2D surface of the internal support, and having cavities 170.

Tissue-Engineered Construct

The tissue/organ replacement of the present technology includes a tissue-engineered construct that includes one or more bio ink compositions. In any embodiment herein, the tissue-engineered construct may be configured to have any suitable shape or size. For example, in any embodiment herein, the tissue-engineered construct may have a customized 3D structure of various shapes and sizes for a number of clinical applications, such as facial or craniofacial applications, engineered cartilage tissue, or combinations thereof. In any embodiment herein, the tissue-engineered construct may have a shape of an organ or tissue of a subject. For example, in any embodiment herein the organ or tissue is selected from an ear, a nose, meniscus, articular cartilage, or a heart valve. In any embodiment herein, the organ is an ear. FIG. 1A shows an embodiment of a tissue-engineered construct 140 having the shape of a human ear, where the helix of the ear is partially covered by an external support 120 according to an embodiment of the present technology and contoured portions of the tissue-engineered "ear shaped" construct partially encapsulates an internal support 130.

In any embodiment herein, the tissue-engineered construct may have a 3D structure based on a 3D computer model. For example, in any embodiment herein, the computer based model may include a 3D contralateral organ or tissue of a subject. In any embodiment herein, the subject is a mammal (e.g., a cat, dog, rodent, or primate). In any embodiment herein, the subject is a human. The computer based 3D model may be obtained via 3D imaging tools. Suitable 3D imaging tools include, but are not limited to, clinical computed tomography (CT), magnetic resonance imaging (MM), laser scanning, 3D cameras, or combinations of any two or more thereof.

The tissue-engineered construct may be configured such that the size of the tissue-engineered construct is greater than the size of the biocompatible support structure, where the tissue-engineered construct is partially or fully in contact with the biocompatible support structure. For example, in any embodiment herein, the tissue-engineered construct may be configured such that the internal supports of the biocompatible support structure are fully or partially encapsulated within the tissue-engineered construct.

In any embodiment herein, the tissue-engineered construct may be configured such that size of the tissue-engineered construct is smaller than the biocompatible support, where the tissue-engineered construct is fully or partially covered and/or enclosed by the external supports of the biocompatible support structure. For example, in any embodiment herein, one or more 2D outer surfaces of the tissue-engineered construct may be covered and/or enclosed by the external support of the biocompatible support structure. In any embodiment herein, the tissue-engineered construct may have a size that exceeds the capacity of the external support of the biocompatible support structure such that the tissue-engineered construct extends (or protrudes) beyond an outer 2D surface of the external support. For example, in any embodiment herein, the tissue-engineered construct may extend (or protrude) through the one or more apertures of the external support of the biocompatible support structure.

In any embodiment herein, the tissue-engineered construct may include a unique set of mechanical properties to enable its proper function. For example, in any embodiment herein, the tissue-engineered construct may have one or more of an equilibrium modulus of about 2 kPa to about 2 MPa, an instantaneous modulus of about 20 kPa to about 20 MPa, and a hydraulic permeability of about $1\times10^{-16}$ $m^2$/Pa·s to about $1\times10^{-8}$ $m^2$/Pa·s. In any embodiment herein, the tissue-engineered construct may have an equilibrium modulus of about 2 kPa to about 2 MPa, about 2 kPa to about 1.5 MPa, about 2 kPa to about 1 MPa, about 2 kPa to about 800 kPa, about 2 kPa to about 600 kPa, about 2 kPa to about 400 kPa, or any range including and/or in between any two of the preceding values. For example, in any embodiment herein, the equilibrium modulus may be 2 kPa, about 10 kPa, about 25 kPa, about 50 kPa, about 100 kPa, about 200 kPa, about 300 kPa, about 400 kPa, about 500 kPa, about 600 kPa, about 700 kPa, about 800 kPa, about 900 kPa, about 1 MPa, about 1.1 MPa, about 1.2 MPa, about 1.3 MPa, about 1.4 MPa, about 1.5 MPa, about 1.6 MPa, about 1.7 MPa, about 1.8 MPa, about 1.9 MPa, about 2 MPa or any range including and/or in between any two of the preceding values.

In any embodiment herein, the tissue-engineered construct may have an instantaneous modulus of about 20 kPa to about 20 MPa, 50 kPa to about 15 MPa, about 100 kPa to about 10 MPa, about 500 kPa to about 8 MPa, about 1 MPa to about 5 MPa, or any range including and/or in between any two of the preceding values. For example, in any embodiment herein, the tissue engineered construct may have an instantaneous modulus of about 20 kPa, about 40 kPa, about 60 kPa, about 80 kPa, about 100 kPa, about 200 kPa about 300 kPa, about 400 kPa, about 500 kPa, about 600 kPa, about 700 kPa, about 800 kPa, about 900 kPa, about 1 MPa, about 2 MPa, about 3 MPa, about 4 MPa, about 5 MPa, about 6 MPa, about 7 MPa, about 8 MPa, about 9 MPa, about 10 MPa, about 11 MPa, about 12 MPa, about 13 MPa, about 14 MPa, about 15 MPa, about 16 MPa, about 17 MPa, about 18 MPa, about 19 MPa, about 20 MPa, or any range including and/or in between any two of the preceding values. In any embodiment herein, the tissue-engineered construct may have a hydraulic permeability of about $1\times10^{-16}$ $m^2$/Pa·s to about $1\times10^{-8}$ $m^2$/Pa·s, about $1\times10^{-13}$ $m^2$/Pa·s to about $9\times10^{-10}$ $m^2$/Pa·s, about $1\times10^{-12}$ $m^2$/Pa·s to about $6\times10^{-10}$, about $1\times10^{11}$ $m^2$/Pa·s to about $3\times10^{10}$ $m^2$/Pa·s, or any range including and/or in between any two of the preceding values.

The tissue-engineered construct may include one or more bio ink compositions. The term "bio ink" or "bio ink composition" refers to an ink derived from biomaterial. For example, in any embodiment herein, the bio ink may include, but is not limited to, hydrogel (e.g., alginate hydrogel), hyaluronic acid, elastin, laminin, agarose, collagen, chitosan, fibrin, hyaluronic acid, carrageenan, polyethylene oxide, polypropylene oxide, polyethylene oxide-co-polypropylene oxide, hydroxypropyl methyl cellulose, poly(propylene fumarate-co-ethylene glycol), poly(ethylene glycol)-co-poly(lactic acid), poly(vinyl alcohol), KDLl 2 oligopeptides, poly(n-isopropyl acrylamide), or combinations of two or more thereof. The bio ink may have a controlled rate of crosslinking through the adjustment of environmental variables including, but not limited to, temperature, pH, ionic strength, heat, UV light, or the addition of chemical crosslinking agents such as calcium, magnesium, barium, chondroitin, sulfate, carbodiimides, ribose, riboflavin, and thrombin. Suitable hydrogels for use in bio inks for tissue-engineered constructs are described in U.S. Pat. No. 9,044,335 entitled "COMPOSITE TISSUE-ENGINEERED INTERVERTEBRAL DISC WITH SELF-ASSEMBLED ANNULAR ALIGNMENT," filed on May 5, 2010, the entire contents of which are hereby incorporated by reference.

In any embodiment herein, the one or more bio ink compositions of the tissue-engineered construct may include alginate hydrogel. For example, in any embodiment herein, the alginate hydrogel may be present in an amount from about 0.5% (w/v) to about 10% (w/v). For example, in any embodiment herein, the alginate hydrogel may be present in an amount of about 0.5% (w/v), about 0.6% (w/v), about 0.7% (w/v), about 0.8% (w/v), about 0.9% (w/v), about 1.0% (w/v), about 1.5% (w/v), about 2.0% (w/v), about 2.5% (w/v), about 3.0% (w/v), about 3.5% (w/v), about 4.0% (w/v), about 4.5% (w/v), about 5.0% (w/v), about 5.0% (w/v), about 5.5% (w/v), about 6.0% (w/v), about 6.5% (w/v), about 7.0% (w/v), about 7.5% (w/v), about 8.0% (w/v), about 8.5% (w/v), about 9.0% (w/v), about 9.5% (w/v), about 10.0% (w/v), or any range including and/or in between any two the preceding values.

In any embodiment herein, the one or more bio ink compositions of the tissue-engineered construct may include collagen. Collagen-based materials are advantageous for use in tissue-engineered constructs. Methods of harvesting collagen for use in bio gel compositions, methods for making 3D structures using bio gel compositions, and methods for preparing bio gel compositions for use in 3D printing systems are described in PCT Application Serial No. PCT/US2017/034582 entitled "3D PRINTABLE BIO GEL AND METHOD OF USE," filed on May 25, 2017, the entire contents of which are hereby incorporated by reference for the background information and methods set forth therein.

In any embodiment herein, the one or more bio ink compositions of the tissue-engineered construct may include collagen in an amount greater than about 5 mg/ml. Suitable amounts of collagen in the bio ink may include, but are not limited to, about 5 mg/ml to about 200 mg/ml. For example, in any embodiment herein, the collagen may be present in an amount of about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, about 155 mg/ml, about 160 mg/ml, about 165 mg/ml, about 170 mg/ml, about 175 mg/ml, about 180 mg/ml, about 185 mg/ml, about 190 mg/ml, about 195 mg/ml, about 200 mg/ml, or any range including and/or in between any two of the preceding values.

In any embodiment herein, the tissue-engineered construct may include one or more bio ink compositions having type I collagen, type III collagen, type IV collagen, other fibrillary collagens, or a combination thereof In any embodiment herein, the one or more bio ink compositions of the tissue-engineered construct may further include a neutralizer and cellular media as described herein in any embodiment. Suitable neutralizers may include, but are not limited to, formulations containing weak acid, for instance. In any embodiment herein, the tissue-engineered construct may be cellular or acellular. For example, in any embodiment herein, the bio ink of the tissue-engineered construct may include cellular media containing a population of cells which may include, but are not limited to, living cells obtained and/or isolated from tissue subject. The cellular media may further include other living cells; for example, in any embodiment herein, the bio ink may include epidermal cells, chondrocytes and other cells that form mesenchymal stem cells, adipose derived stem cells, cartilage, macrophages, adipocytes, dermal cells, muscle cells, hair follicles, fibroblasts, organ cells, osteoblasts, osteocytes and other cells that form bone, endothelial cells, mucosal cells, pleural cells, ear canal cells, tympanic membrane cells, peritoneal cells, Schwann cells, corneal epithelial cells, gingiva cells, central nervous system neural stem cells, tracheal epithelial cells, or combinations of two or more thereof.

In any embodiment herein, the population of cells may be present in an amount from about $1.0\times10^5$ cells/ml to about $5.0\times10^7$ cells/ml. For example, in any embodiment herein, the amount of cells present in the bio ink of the tissue-engineered construct may include about $1.0\times10^5$ cells/ml, about $2.0\times10^5$ cells/ml, about $3.0\times10^5$ cells/ml, about $4.0\times10^5$ cells/ml, about $5.0\times10^5$ cells/ml, about $6.0\times10^5$ cells/ml, about $7.0\times10^5$ cells/ml, about $8.0\times10^5$ cells/ml, about $9.0\times10^5$ cells/ml, about $1.0\times10^6$ cells/ml, about $2.0\times10^6$ cells/ml, about $3.0\times10^6$ cells/ml, about $4.0\times10^6$ cells/ml, about $5.0\times10^6$ cells/ml, about $6.0\times10^6$ cells/ml, about $7.0\times10^6$ cells/ml, about $8.0\times10^6$ cells/ml, about $9.0\times10^6$ cells/ml, about $1.0\times10^7$ cells/ml, about $2.0\times10^7$ cells/ml, about $3.0\times10^7$ cells/ml, about $4.0\times10^7$ cells/ml, about $5.0\times10^7$ cells/ml, or any range including and/or in between any two of the preceding values. Suitable amounts of cells present in the bio ink of the tissue-engineered construct include, but are not limited to about $1.0\times10^5$ cells/ml to about $5.0\times10^7$ cells/ml, about $1.0\times10^5$ cells/ml to about $1.0\times10^7$ cells/ml, about $1.0\times10^5$ cells/ml to about $5.0\times10^6$ cells/ml, about $1.0\times10^5$ cells/ml to about $5.0\times10^6$ cells/ml, or any range including and/or in between any two of the preceding values.

In any embodiment herein, the one or more bio ink compositions of the tissue-engineered construct may be acellular, where the bio ink does not contain living cells. In any embodiment herein, the tissue-engineered construct may be configured such that the tissue-engineered construct has areas or components that may be acellular or cellular. For example, the tissue-engineered construct may include a volume of a bio ink composition fully or partially encapsulated within an internal support separating the volume of bio ink composition from other portions of the tissue-engineered construct. In any embodiment herein, the volume of encapsulated bio ink composition may be different than the non-encapsulated bio ink of the tissue-engineered construct. For example, in any embodiment herein, the tissue-engineered construct may include multiple volumes of the same or different bio ink compositions encapsulated by two or more internal supports. Here, the tissue-engineered construct includes multiple bio ink compositions.

In any embodiment herein, the one or more bio ink compositions of the tissue-engineered construct may further include carriers or additives. Suitable carriers may include, but are not limited to, water, aqueous ionic salt solutions (e.g., saline), phosphate buffer saline (PBS), cell medium, fetal bovine serum (FBS), Dulbecco's minimum essential medium (DMEM), fibroblast growth factor (bFGF), or the like or combinations thereof. Suitable additives include, but are not limited to, growth factors and crosslinking agents. Suitable crosslinking agents include, but are not limited to, riboflavin, ribose, polyethylene glycol (PEG), glutaraldehyde, 1-ethyl-3-(3-dimethylaminopropyl)-carbodiimide hydrochloride, genipin, chitosan, or the like or combinations thereof.

Biocompatible Support Structure

The present technology provides a biocompatible support structure that includes one or more external supports, internal supports, or a combination thereof of a biocompatible material. FIG. 1B shows an embodiment of a biocompatible support structure 110 having an external support 120 and an internal support 130, wherein the internal support is connected to one or more 2D surfaces of the external support. As used herein, "external supports" refers to one or more structural components customized into various 2D or 3D shapes and sizes and configured to serve as an exoskeletal structure covering one or more surfaces of the tissue-engineered construct. FIG. 1C shows an external support 120 configured to cover the helix of an ear shaped tissue-engineered construct. For example, in any embodiment herein, the external support may completely encapsulate the tissue-engineered construct such that the external support fully covers the outer surfaces of the tissue-engineered construct. In any embodiment herein, the external support may partially cover one or more outer surfaces of the tissue-engineered construct. FIG. 1A shows an embodiment of an external support 120 partially covering the helix portion of a human ear shaped tissue-engineered construct 140. In any embodiment herein, the external support may include one or more cavities (i.e., openings) to allow the flow of materials (e.g., nutrients, biological waste material, cellular and tissue materials, for example, growing vascular and nerve structures, or the like or combinations thereof), where the cavity houses the tissue-engineered construct.

As used herein, "internal support" refers to one or more structural components customized into various 2D or 3D shapes and sizes and configured to serve as an internal skeletal structure that is fully or partially encapsulated by the tissue-engineered construct. For example, in any embodiment herein, the internal support may be fully encapsulated by the tissue-engineered construct such that no portion of the internal support extends beyond a 2D outer surfaces of the tissue-engineered construct. In any embodiment herein, the internal support may be partially encapsulated by the tissue-engineered structure such that one or more portions of the internal support extends beyond one or more 2D outer surfaces of the tissue-engineered construct. In any embodiment herein, the internal support may be connected to and extend distally from one or more 2D surfaces of the external support. In any embodiment herein, the internal support may include one or more cavities (i.e., openings) to allow the flow of materials (e.g., nutrients, biological waste material, cellular and tissue materials, for example, growing vascular and nerve structures, or the like or combinations thereof), where the cavity may include a volume of a bio ink composition that is the same or different than a bio ink not in the cavity. FIG. 1D shows an internal support 130 having a cavity 170.

In any embodiment herein, the internal support may have a 2D or 3D shape such that it occupies a volume of space within the tissue-engineered construct that is less than the total volume of the tissue-engineered construct. For example, in any embodiment herein, the internal support may fully or partially degrade, absorb, or resorb to form one or more cavities, channels, or combinations thereof in the tissue-engineered construct. In any embodiment herein, the one or more cavities and/or channels may be fully encapsulated by the tissue-engineered construct such that the unfilled cavity and/or channel does not extend beyond a 2D outer surface of the tissue-engineered construct. In any embodiment herein, the one or more cavities and/or channels may extend beyond one or more 2D outer surfaces of the tissue-engineered construct. For example, in any embodiment herein, the cavity and/or channel may extend there-through such that one 2D outer surface of the tissue-engineered construct is in fluid communication with a different 2D outer surface of the tissue-engineered construct. In any embodiment herein, the one or more cavities and/or channels may extend beyond one 2D outer surface of the tissue-engineered construct such that there is no fluid communication to a different 2D outer surface of the tissue-engineered construct. In any embodiment herein, the one or more cavities and/or channels may be filled with or allow the flow of materials (e.g., nutrients, biological waste material, cellular and tissue materials, or the like or combinations thereof).

In any embodiment herein, the internal support may be configured to full or partially encapsulate a volume of a bio ink composition within the tissue-engineered construct. Here, the internal supports form one or more separate pockets of fully or partially encapsulated bio ink composition within the tissue-engineered construct. For example, the volume of bio ink composition encapsulated by the internal support may be the same or a different from the bio ink composition not encapsulated by the internal support. In any embodiment herein, the volume of bio ink composition encapsulated by the internal support is different than the non-encapsulated bio ink of the tissue-engineered construct.

Without being bound by theory, it is believed that the external support and/or internal support bolster the stiffness of the tissue-engineered construct. In addition, the external and/or internal support may further bolster the compression modulus, tension modulus, flexural stiffness, and shear strength. It can limit shape distortion when there is externally applied compression by confining the bio material. For example, the supports add to axial and bending stiffness and other mechanical properties as described herein of the tissue-engineered constructs by providing in some cases a stiffer material internally and for external supports this is achieved with minimal material due to the increase in the cross sectional moment of inertia. In any embodiment herein, the one or more external supports, internal supports, or combinations thereof of the biocompatible support structure increases one or more of axial and bending stiffness, compression modulus, tension modulus, flexural stiffness, and shear strength of the tissue-engineered construct by 5 times to about 10,000 times. For example, in any embodiment herein, the axial and bending stiffness, compression modulus, tension modulus, flexural stiffness, and shear strength may be increased by about 5 times, about 10 times, about 20 times, about 30 times, about 40 times, about 50 times, about 60 times, about 70 times, about 80 times, about 90 times, about 100 times, about 200 times, about 300 times, about 400 times, about 500 times, about 1000 times, about 5000 times, about 10,000 times, or any range including and/or in between any two of the preceding values.

In any embodiment herein, the one more external supports, internal supports, or combinations thereof have a two-dimensional "2D" thickness suitable to achieve the desired mechanical properties, such as the flexural modulus of the biocompatible support or imparting the desired tensile, compressive and bending mechanical properties, and load capacity to the tissue-engineered construct. For example, in any embodiment herein, the external supports or internal supports have a 2D thickness of about 10 μm to about 2000 μm. For example, in any embodiment herein, the external supports or internal supports may have a 2D thickness of about 10 μm, about 20 μm, about 30 μm, about 40 μm, about 50 μm, about 60 μm, about 70 μm, about 80 μm, about 90 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1000 μm, about 1050 μm, about 1100 μm, about 1150 μm, about 1200 μm, about 1250 μm, about 1300 μm, about 1350 μm, about 1400 μm, about 1450 μm, about 1500 μm, about 1550 μm, about 1600 μm, about 1650 μm, about 1700 μm, about 1750 μm, about 1800 μm, about 1850 μm, about 1900 μm, about 1950 μm, about 2000 μm, or any range including and/or in between any of the preceding values. Suitable 2D thicknesses include, but are not limited to, from about 10 μm to about 2000 μm, about 10 μm to about 1500 μm, about 10 μm to about 1000 μm, about 10 μm to about 500 μm, or ranges including and/or in between any of the preceding values.

In any embodiment herein, the external supports or internal supports may include one or more apertures extending there-through from one 2D surface to an opposing parallel surface of the external support and/or internal support allowing for the flow of materials (e.g., nutrients, biological waste material, cellular and tissue materials, or the like or combinations thereof). FIG. 1C shows an external support 120 having one or more apertures 150, and FIG. 1D shows an internal support having one or more apertures 160. The one or more apertures may have an average size in a range from about 1 μm to about 10,000 μm. In any embodiment herein, the average size of the one or more apertures may include, but is not limited to, about 1 μm, about 5 μm, about 10 μm, about 20 μm, about 30 μm, about 40 μm, about 50 μm, about 60 μm, about 70 μm, about 80 μm, about 90 μm, about 100, about 200 μm, about 300 μm, about 400 μm, about 500 μm, about 600 μm, about 700 μm, about 800 μm, about 900 μm, about 1000 μm, about 1500 μm, about 2000 μm, about 2500 μm, about 3000 μm, about 3500 μm, about 4000 μm, about 4500 μm, about 5000 μm, about 5500 μm, about 6000 μm, about 6500 μm, about 7000 μm, about 7500 μm about 8000 μm, about 8500 μm, about 9000 μm, about 9500 μm, about 10,000 μm, or any range including and/or in between any two of the preceding values. Suitable ranges include from about 1 μm to about 10,000 μm, about 5 μm to about 7500 μm, about 10 μm to about 7000 μm, about 20 μm to about 5000 μm, about 35 μm to about 2500 μm, or ranges including and/or in between any two of the preceding values. The one or more apertures may have any shape; for example, the shape of the one or more apertures may be circular, ovular, elliptical, polygonal, or the like or combinations thereof.

In any embodiment herein, one or more surfaces of the external support and/or internal support may include one or more appendage elements connected to and extending distally from the one or more 2D surfaces of the external support and/or internal support. For example, in any embodiment herein, the appendage elements may include, but are not limited to, spikes, nodules, nodes, struts, ridges, or the like or combinations thereof.

In any embodiment herein, the biocompatible support structure may include any combination of the external supports and/or internal supports. For example, the biocompatible support structure may include only the one or more external supports as described herein in any embodiment. The biocompatible support, in any embodiment herein, may include only the one or more internal supports. In any embodiment herein, the biocompatible support structure may include one or more external supports and one or more internal supports. For example, a portion of the internal support may be connected to a 2D surface of the external support. In any embodiment herein, the biocompatible support structure may include the external support and internal support, where the one or more external supports do not connect or are not in contact with the one or more internal supports.

The biocompatible support structure may include a biocompatible material. For example, in any embodiment herein, the biocompatible material may include, but is not limited to, polysaccharides, biocompatible polymers, rubber, silicon, biocompatible metals (e.g., steel, cobalt-chromium alloys, titanium, titanium alloys magnesium, magnesium alloys, zinc, zinc alloys, iron alloys, or the like or combinations thereof), biocompatible ceramics, polyethylene glycol, polypropylene glycol, poly amino acids, natural and biopolymers (e.g., glycosaminoglycans, cellulose, chitosan, chitin, dextrans, gelatin, collagen, lignins, polyamino acids, glycoproteins, elastin, laminins), or combinations of two or more thereof. In any embodiment, the biocompatible material may include biocompatible polymers; for example, in any embodiment herein, the biocompatible polymers may include polylactides (PLA), polyglycolides acid (PGA), poly (lactide-co-glycolide) (PLGA), polydioxanone (PDO), polycaprolactones, and combinations thereof.

In any embodiment herein, the biocompatible polymer may have a melting point between about 50° C. to about 290° C. For example, in any embodiment herein, the biocompatible polymer may have a melting point of about 50° C., about 55° C., about 60° C., about 65° C., about 70° C., about 75° C., about 80° C., about 85° C., about 90° C., about 95° C., about 100° C., about 110° C., about 120° C., about 130° C., about 140° C., about 150° C., about 160° C., about 170° C., about 180° C., about 190° C., about 200° C., about 210° C., about 220° C., about 230° C., about 240° C., about 250° C., about 260° C., about 270° C., about 280° C., about 290° C., or any range including and/or in between any two of the preceding values.

In any embodiment herein, the biocompatible material may further include one or more additives. For example, the one or more additives may include, but are not limited to crosslinking agents.

The biocompatible material may be biodegradable, bioabsorbable, bioresorbable, or a combination thereof. For example, in any embodiment herein, the biocompatible material may degrade, absorb, or resorb under physiological conditions at a rate of from about 1 week to about 7 years. Suitable rates of degradation, absorption, or resorption may include, but are not limited to, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 2.5 years, about 3 years, about 3.5 years, about 4 years, about 4.5 years, about 5 years, about 5.5 years, about 6 years, about 6.5 years, about 7 years, or ranges including and/or in between any two of the preceding values. For example, in any embodiment herein, the rate of degradation, absorption, or resorption may include about 1 week to about 7 years, about 1 week to about 5 years, about 1 week to about 3 years, about 1 week to about 1 year, about 1 week to about 6 months, about 1 week to about 3 months. Suitable biodegradable, bioabsorbable, and/or bioresorbable materials include, but are not limited to, include, but are not limited to, PLA, PGA, PLGA, PDO, polycaprolactones, bioresorbable metal alloys, and combinations thereof.

In any embodiment herein, the internal support may be a different biomaterial than the external support material. For example, the internal support may be a biomaterial having a rate of degradation, absorption, or resorption that is different than the external support. In any embodiment herein, the biomaterial of the internal support has a rate of degradation, absorption, or resorption that is longer than the external support. In any embodiment herein, the biomaterial of the internal support has a rate of degradation, absorption, or resorption that is shorter than the external support.

When the material is or includes a biopolymer, protein, glycoprotein (e.g., as listed above) the concentration of that component may be about 1000 mg/ml to about 2500 mg/ml. For example, in any embodiment herein, the biocompatible material may be present in a concentration of about 1000 mg/ml, about 1100 mg/ml, about 1200 mg/ml, about 1300 mg/ml, about 1400 mg/ml, about 1500 mg/ml, about 1600 mg/ml, about 1700 mg/ml, about 1800 mg/ml, about 1900 mg/ml, about 2000 mg/ml, about 2100 mg/ml, about 2200 mg/ml, about 2300 mg/ml, about 2400 mg/ml, about 2500 mg/ml, or any range including and/or between any two of the preceding values. In any embodiment herein, the biocompatible material may be present at a concentration of about 1500 mg/ml to about 2500 mg/ml, about 1750 mg/ml to about 2200 mg/ml, about 2000 mg/ml to about 2300 mg/ml, or any range including and/or in between any two of the preceding values.

The biocompatible material may be present in the biocompatible support structure in an amount of about 1% by weight to 100% by weight of the biocompatible support structure. For example, in any embodiment herein, the amount of biocompatible material present by weight in the biocompatible support structure may be about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or any range including and/or in between any two of the preceding values. Suitable amounts of the bio compatible material in the biocompatible support include, but are not limited to, about 5% to about 100%, 10% to about 100%, about 50% to about 100%, about 5% to about 20%, about 90% to about 100%, or any range including and/or in between any two of the preceding values.

The biocompatible support structure has mechanical properties allowing it to bolster the mechanical properties of the tissue-engineered construct. In any embodiment herein, the biocompatible support structure may have one or more of a flexural modulus of about 0.2 GPa to about 100 GPa, a modulus of elasticity of about 0.02 GPa to about 100 GPa, or a tensile strength of about 1 MPa to about 1000 MPa.

In any embodiment herein, the biocompatible support structure may have a flexural modulus of about 0.2 GPa to about 100 GPa. For example, in any embodiment herein, the biocompatible support structure may have a flexural modulus of about 0.2 GPa, about 0.3 GPa, about 0.4 GPa, about 0.5 GPa, about 0.6 GPa, about 0.7 GPa, about 0.8 GPa, about 0.9 GPa, about 1 GPa, about 2 GPa, about 3 GPa, about 4 GPa, about 5 GPa, about 6 GPa, about 7 GPa, about 8 GPa, about 9 GPa, about 10 GPa, about 11 GPa, about 12 GPa, about 13 GPa, about 14 GPa, about 15 GPa, about 16 GPa, about 17 GPa, about 18 GPa, about 19 GPa, about 20 GPa, about 25 GPa, about 30 GPa, about 35 GPa, about 40 GPa, about 45 GPa, about 50 GPa, about 55 GPa, about 60 GPa, about 65 GPa, about 70 GPa, about 75 GPa, about 80 GPa, about 85 GPa, about 90 GPa, about 95 GPa, about 100 GPa, or any range including and/or in between any two of the preceding values. Suitable flexural modulus values may include, but are not limited to about 0.2 GPa to about 100 GPa, about 0.2 GPa to about 50 GPa, about 0.2 GPa to about 25 GPa, about 0.2 GPa to about 15 GPa, about 1 GPa to about 15 GPa, about 5 GPa to about 15 GPa, or ranges including and/or in between any two of these values.

In any embodiment herein, the biocompatible support structure may have a modulus of elasticity of about 0.02 GPa to about 100 GPa. For example, in any embodiment herein, the biocompatible support structure may have a modulus of elasticity of about 0.02 GPa, 0.04 GPa, about 0.06 GPa, about 0.08 GPa, about 0.1 GPa, about 0.2 GPa, about 0.3 GPa, about 0.4 GPa, about 0.5 GPa, about 0.6 GPa, about 0.7 GPa, about 0.8 GPa, about 0.9 GPa, about 1 GPa, about 2 GPa, about 3 GPa, about 4 GPa, about 5 GPa, about 6 GPa, about 7 GPa, about 8 GPa, about 9 GPa, about 10 GPa, about 11 GPa, about 12 GPa, about 13 GPa, about 14 GPa, about 15 GPa, about 16 GPa, about 17 GPa, about 18 GPa, about 19 GPa, about 20 GPa, about 25 GPa, about 30 GPa, about 35 GPa, about 40 GPa, about 45 GPa, about 50 GPa, about 55 GPa, about 60 GPa, about 65 GPa, about 70 GPa, about 75 GPa, about 80 GPa, about 85 GPa, about 90 GPa, about 95 GPa, about 100 GPa, or any range including and/or in between any two of the preceding values. Suitable modulus of elasticity values may include, but are not limited to about 0.2 GPa to about 100 GPa, about 0.2 GPa to about 50 GPa, about 0.2 GPa to about 25 GPa, about 0.2 GPa to about 15 GPa, about 1 GPa to about 15 GPa, about 5 GPa to about 15 GPa, or ranges including and/or in between any two of these values.

In any embodiment herein, the biocompatible support structure may have a tensile strength of about 1 MPa to about 1000 MPa. For example, in any embodiment herein, the biocompatible support structure may have a tensile strength of about 1 MPa, about 2 MPa, about 3 MPa, about 4 MPa, about 5 MPa, about 6 MPa, about 7 MPa, about 8 MPa, about 9 MPa, about 10 MPa, about 20 MPa, about 25 MPa, about 30 MPa, about 35 MPa, about 40 MPa, about 45 MPa, about 50 MPa, about 55 MPa, about 60 MPa, about 65 MPa, about 70 MPa, about 75 MPa, about 80 MPa, about 85 MPa, about 90 MPa, about 95 MPa, about 100 MPa, about 150 MPa, about 200 MPa, about 250 MPa, about 300 MPa, about 350 MPa, about 400 MPa, about 450 MPa, about 500 MPa, about 550 MPa, about 600 MPa, about 650 MPa, about 700 MPa, about 750 MPa, about 800 MPa, about 850 MPa, about 900 MPa, about 950 MPa, about 1000 MPa, or ranges including and/or in between any two of the preceding values.

The tissue or organ replacement composition includes the tissue-engineered construct and biocompatible support structure together, in any configuration as disclosed herein, and possesses improved mechanical properties (e.g., strength).

In any embodiment herein, the one or more external supports, internal supports, or combinations thereof of the biocompatible support structure may increase load capacity of the tissue-engineered construct by about 1% to about 10,000%. For example, in any embodiment herein, the load capacity of the tissue-engineered construct may be increased by about 1% to about 10,000%, about 1% to about 1,000%, about 1% to about 100%, about 1% to about 10%, or any range including and/or in between any two of the preceding values. Suitable increases in load capacity may include, but are not limited to, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1,000%, about 2,000%, about 3,000%, about 4,000%, about 5,000%, about 6,000%, about 7,000%, about 8,000%, about 9,000%, about 10,000%, or any range including and/or in between any two of the preceding values.

The tissue or organ replacement composition, in any embodiment herein, may withstand compression of about 1 kN to about 10,000 kN and a shear force of about 0.2 kN to about 1,000 kN. For example, in any embodiment herein, the tissue or organ replacement composition of the present technology may withstand compression of about 1 kN, 2 kN, about 3, kN, about 4 kN, about 5 kN, about 6 kN, about 7 kN, about 8 kN, about 9 kN, about 10 kN, about 20 kN, about 30 kN, about 40 kN, about 50 kN, about 60 kN, about 70 kN, about 80 kN, about 90 kN, about 100 kN, about 200 kN, about 300 kN, about 400 kN, about 500 kN, about 600 kN, about 700 kN, about 800 kN, about 900 kN, about 1000 kN, about 1500 kN, about 2000 kN, about 2500 kN, about 3000 kN, about 3500 kN, about 4000 kN, about 4500 kN, about 5000 kN, about 5500 kN, about 6000 kN, about 6500 kN, about 7000 kN, about 7500 kN, about 8000 kN, about 8500 kN, about 9000 kN, about 9500 kN, about 10,000 kN, or ranges including and/or in between any two of the preceding values. Suitable compression ranges may include but are not limited to about 1 kN to about 10,000 kN, about 1 kN to about 5000 kN, about 1 kN to about 1000 kN, about 1 kN to about 500 kN, about 1 kN to about 15 kN, about 4 kN to about 10 kN, or ranges including and/or in between any two of the preceding values.

In any embodiment herein, the tissue or organ replacement composition of the present technology may withstand a shear force of about 0.2 kN to about 1,000 kN. For example, in any embodiment herein, the tissue or organ replacement composition of the present technology may withstand a shear force may be about 0.2 kN, about 0.3 kN, about 0.4 kN, about 0.5 kN, about 0.6 kN, about 0.7 kN, about 0.8 kN, about 0.9 kN, about 1.0 kN, about 10 kN, about 50 kN, about 100 kN, about 150 kN, about 200 kN, about 250 kN, about 300 kN, about 350 kN, about 400 kN, about 450 kN, about 500 kN, about 550 kN, about 600 kN, about 650 kN, about 700 kN, about 750 kN, about 800 kN, about 850 kN, about 900 kN, about 950 kN, about 1000 kN, or ranges including and/or in between any two of the preceding values. Suitable ranges of the shear force include, but are not limited to, about 0.2 kN to about 1000 kN, about 1 kN to about 500 kN, about 10 kN to about 100 kN, about 0.2 kN to about 0.9 kN, or ranges including and/or in between any two of the preceding values.

Methods

The present technology provides a method of fabricating the tissue or organ replacement composition that includes fabricating a biocompatible support structure as described herein in any embodiment; fabricating a tissue-engineered construct as described herein in any embodiment comprising: depositing one or more bio ink compositions as described herein in any embodiment in or around the biocompatible support structure; crosslinking the one or more bio ink compositions, and optionally repeating the depositing and crosslinking steps, to form the tissue-engineered construct; and curing the tissue or organ replacement composition; where the biocompatible support structure includes one or more of external supports, internal supports, or combinations thereof of a biocompatible material, and the biocompatible material is present in an amount of about 1% to about 100% by weight of the biocompatible support structure.

Figure 4B:
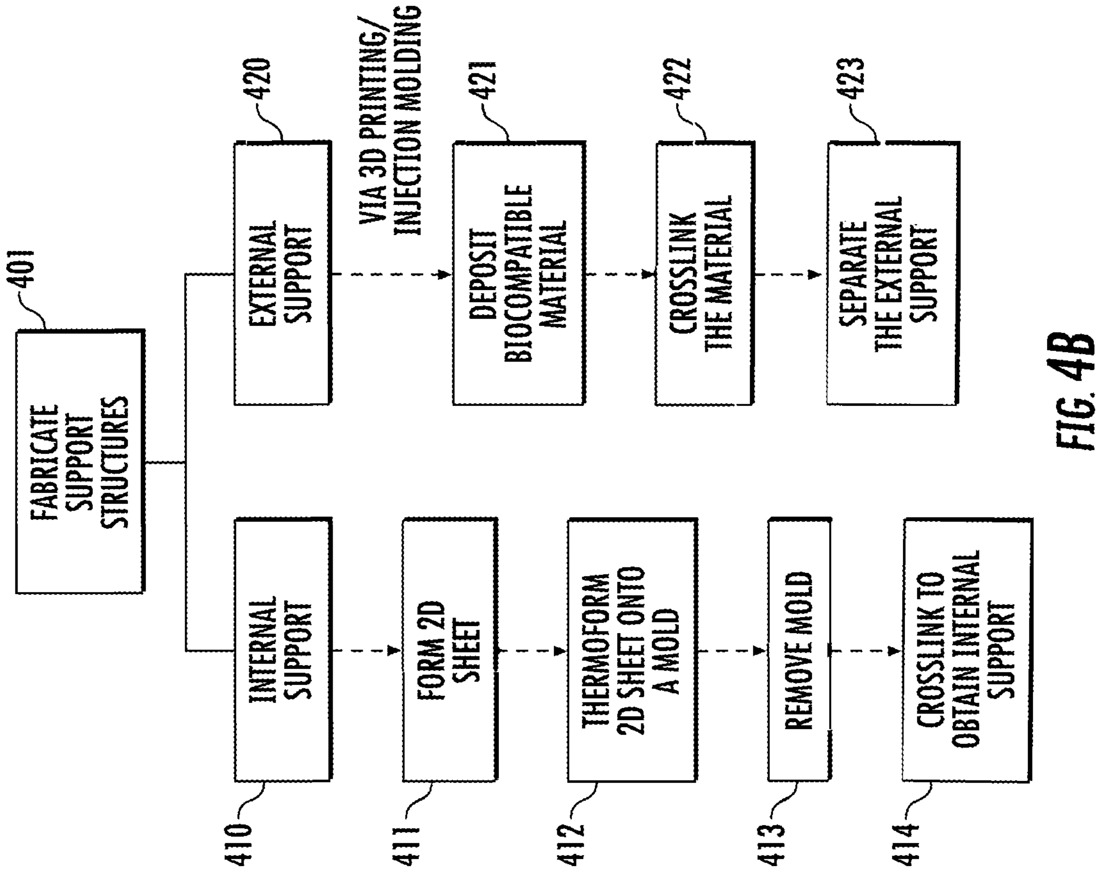
FIGS. 4A-4D show flow diagrams depicting exemplary methods for fabricating a biocompatible support structure and tissue-engineered construct of the tissue or organ replacement composition.
Figure 4A:
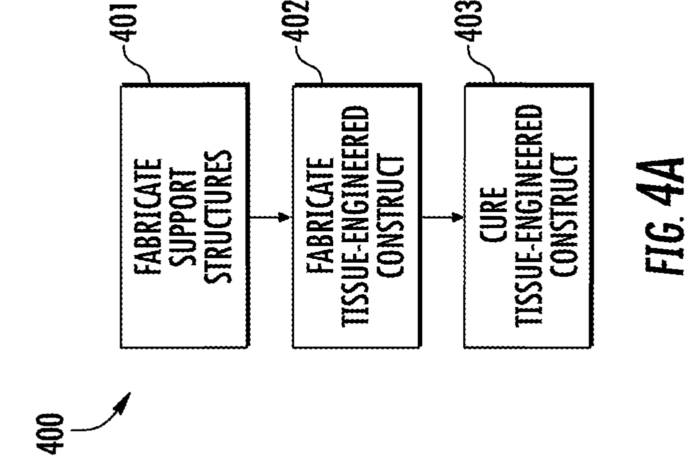

FIG. 4A provides a flow diagram 400 showing an embodiment of the method of fabricating the tissue or organ replacement composition. The method includes fabricating the biocompatible support structures (process 401), fabricating the tissue-engineered construct (process 402), and curing the tissue-engineered construct (process 403). Each of the processes (e.g., subprocesses, subroutines or steps) 401, 402 and 403 is discussed below with reference to FIGS. 4B-4D.

The method of fabricating the biocompatible support structure may include one or more fabrication systems or methods, including but not limited to, thermoforming, injection molding, rotational molding, positive molds, negative molds, extrusion, subtractive manufacturing, cutting, laser cutting, drilling, water jet, punching, direct thermos cutting, chemical etching, selective thermos melting, dipping processes, spray coating, selective electrostatic coating, milling and machining, three-dimensional (3D) printing, or combinations of two more thereof. For example, in any embodiment herein, the method of fabricating may include 3D printing. Suitable 3D printing methods may include, but is not limited to, ink-jet printing, layer-by-layer printing, extrusion printing, or bioprinting. For example, in any embodiment herein, the depositing may include depositing one or more layers of biocompatible material. For example, in any embodiment herein, 3D printing may include: depositing one or more layers of a biocompatible material to a substrate; optionally crosslinking the deposited biocompatible material; and optionally repeating the depositing and optional crosslinking steps to obtain the biocompatible support structure; where the biocompatible support structure includes one or more of external supports, internal supports, or combinations thereof of a biocompatible material, and the biocompatible material is present in an amount of about 1% to about 100% by weight of the biocompatible support structure.

In any embodiment herein, the biocompatible support structure may be fabricated using biocompatible materials as described herein in any embodiment using 3D printing systems as described in PCT Application Serial No. PCT/2018/034457 entitled "ASEPTIC PRINTER SYSTEM INCLUDING DUAL ARM-MECHANISM," filed on May 24, 2018, the entire contents of which are hereby incorporated by reference for the background information and methods set forth therein.

Figure 2A:
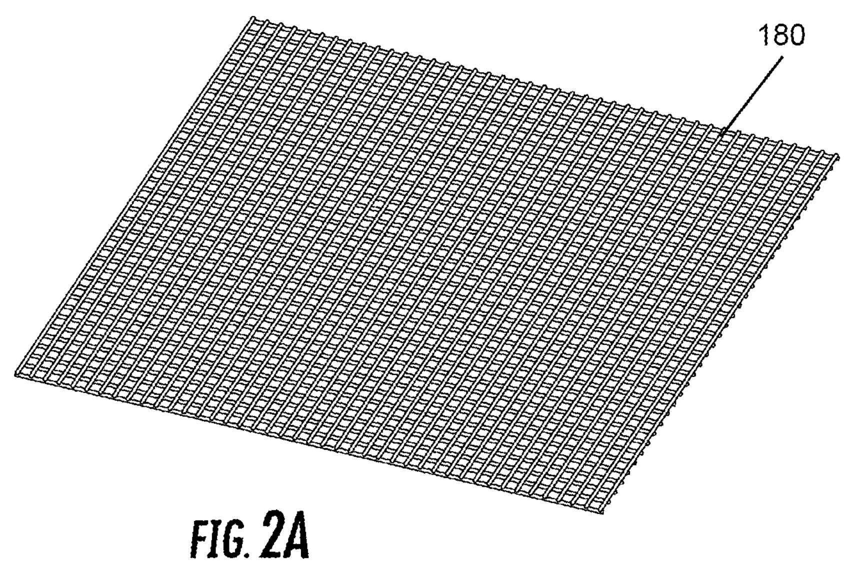
FIG. 2A shows a 2D sheet having one or more apertures according to an embodiment of the present technology.
Figure 2B:
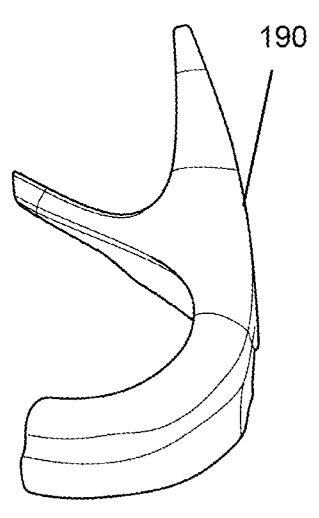
FIG. 2B shows a soluble mold for forming the internal support for an ear shaped tissue-engineered construct according to an embodiment of the present technology.

In any embodiment herein, the method of fabricating the biocompatible support structure may include injection molding. For example, in any embodiment herein, the depositing may include depositing the biocompatible material in a mold of the biocompatible support structure; optionally crosslinking the biocompatible material in the mold, and optionally repeating the depositing and optional crosslinking steps; and removing the biocompatible support structure from the mold. In any embodiment herein, the mold may be soluble or insoluble, such as polymer, metal, or biomaterial. For example, in any embodiment herein, the mold may be soluble such that the mold dissolves to form an internal cavity in the one or more external supports, internal supports, or combinations thereof. In any embodiment herein, the mold may be a soluble material in granular form, such as sand, powder, or the like or combinations thereof. FIG. 2B shows a soluble mold 190 for forming the internal support for an ear shaped tissue-engineered construct.

FIG. 4B provides a flow diagram relating to an embodiment of the method of fabricating an exemplary biocompatible support (process 401) for an internal and/or external support.

In at least one embodiment, the process 401 includes selecting one of an internal support or external support for fabrication. Upon determining to fabricate an internal support (step 410), an exemplary fabrication process includes forming a 2D sheet of the biocompatible material (step 411), thermoforming the 2D sheet onto a mold (step 412), removing the mold (step 413), and crosslinking the biocompatible material to obtain the internal support (step 414).

As further shown in FIG. 4B, upon determining to fabricate an external support (step 420), an exemplary fabrication process includes depositing the biocompatible material via 3D printing or injection molding (step 421), crosslinking the biocompatible material (step 422), and separating the external support from a substrate or mold (e.g., an injection mold) (step 423).

In at least one embodiment, for making an external support, an exemplary technique includes depositing the biocompatible material via a fused deposition process, via a 3D printer or injection molding, and optionally crosslinking the biocompatible material to form the external support. For making an internal support, an exemplary technique includes depositing the biocompatible material to form a 2D sheet, thermoforming the 2D sheet onto a soluble mold, dissolving the mold, and optionally crosslinking the biocompatible material to form the internal support.

Further, in at least one embodiment, a fabrication technique for making a tissue engineered-construct may include depositing bio ink using a 3D bio printer, and may further include placing the biocompatible support structure on a substrate (e.g., a bioprinting buildplate), and depositing the bio ink via printing into and/or around the support structure to obtain an ear shaped tissue-engineered construct. As discussed further herein, the method may include depositing the bio ink using a molding method and may include placing the biocompatible support structure within a tissue-engineered construct mold (e.g., an ear shaped mold), and depositing one or more layers of bio ink into the mold.

Further still, a method of fabricating a tissue-engineered structure according to an embodiment may include a curing process. The curing process may include placing the construct into a media bath (e.g., at about 37° C.) and curing overnight (e.g., for about 12 hours) for 3D printed constructs; or placing the mold into a media bath, removing the construct from the mold after a couple hours (e.g., for about 2 hours), and curing the construct overnight for injection molded constructs.

In any embodiment herein, the method of fabricating the biocompatible support structure may include thermoforming. The method of thermoforming may include any suitable known thermoforming methods, such as methods suitable for thermoforming a porous and/or non-porous 2D sheet. Such thermoforming methods may include heating the 2D sheet and vacuuming onto a mold or heating the 2D sheet and forming with a male and female mold.

Figure 2C:
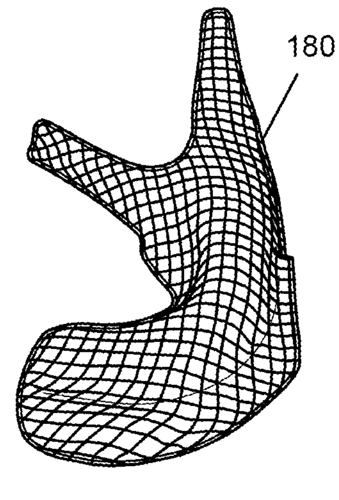
FIG. 2C shows a 2D porous sheet thermoformed onto a mold of an internal support according to an embodiment of the present technology.

For example, in any embodiment herein, the thermoforming includes contacting a 2D sheet of the biocompatible material to a substrate, wherein the substrate includes one or more molds shaped to form the one or more external supports, internal supports, or combinations thereof; heating the 2D sheet of the biocompatible material to thermoform the 2D sheet into conformity with the shape of the one or more molds to obtain the one or more external supports, internal supports, or combinations thereof; and removing the one or more external supports, internal supports, or combinations thereof from the mold. In any embodiment therein, the thermoforming may further include repeating one or more of the contacting, heating, and removing of the one or more molds to obtain a desired shape of the one or more external supports, internal supports, or combinations thereof. FIG. 2C shows a 2D porous sheet thermoformed onto a mold of an internal support.

In any embodiment herein, the 2D sheet may be made from 3D printed, molded, woven, or knitted fibers. For example, in any embodiment herein, the 2D sheet may be 3D printed fibers via 3D printing methods described herein. In any embodiment herein, the 2D sheet may be porous or non-porous. In any embodiment herein, the porous 2D sheet may include one or more apertures having an average size in a range from about 1 μm to about 10,000 μm as described herein in any embodiment. The one or more apertures may have any shape; for example, the shape of the one or more apertures may be circular, ovular, elliptical, polygonal, or the like or combinations thereof. FIG. 2A shows a 2D sheet 180 having one or more apertures according to an embodiment of the present technology.

In any embodiment herein, the fibers may have a diameter of about 10 μm to about 2000 μm. For example, in any embodiment herein, the external supports or internal supports may have a 2D thickness of about 10 μm, about 20 μm, about 30 μm, about 40 μm, about 50 μm, about 60 μm, about 70 μm, about 80 μm, about 90 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1000 μm, about 1050 μm, about 1100 μm, about 1150 μm, about 1200 μm, about 1250 μm, about 1300 μm, about 1350 μm, about 1400 μm, about 1450 μm, about 1500 μm, about 1550 μm, about 1600 μm, about 1650 μm, about 1700 μm, about 1750 μm, about 1800 μm, about 1850 μm, about 1900 μm, about 1950 μm, about 2000 μm, or any range including and/or in between any of the preceding values. Suitable 2D thicknesses include, but are not limited to, from about 10 μm to about 2000 μm, about 10 μm to about 1500 μm, about 10 μm to about 1000 μm, about 10 μm to about 500 μm, or ranges including and/or in between any of the preceding values.

In any embodiment herein, the substrate may include a surface of a 3D printer (e.g., build plate of a 3D printer). In any embodiment herein, the substrate may include a mold suitable for use in one or more of injection molding, rotational molding, positive molds, negative molds, or the like. In any embodiment herein, the substrate may include a surface of a fabrication device suitable for performing subtractive manufacturing, milling and machining, or the like. In any embodiment herein, the substrate may be a mold having the 3D shape of the tissue-engineered construct.

In any embodiment herein, the biocompatible material is crosslinked. For example, in any embodiment herein, the biocompatible material may be subjected to crosslinking conditions to produce a cross-linked or polymerized biocompatible material. Suitable crosslinking conditions may include, but are not limited to, UV exposure. In any embodiment herein, the biocompatible material may not include crosslinking. For example, in any embodiment, following deposition, the biomaterial may include a cooling step, a fusing step, and the like or combinations thereof.

In the method of the present technology, the method of fabricating the biocompatible support structure may include depositing the one or more layers of biocompatible material such that the one or more external supports and/or internal supports have a 2D thickness of about 10 μm to about 2000 μm as described herein in any embodiment.

In the method of the present technology, the biocompatible material may include a biocompatible material as described herein in any embodiment. In any embodiment herein, the biocompatible polymer may have a melting point between about 50° C. to about 290° C. as described herein in any embodiment.

In any embodiment herein, the biocompatible support structure obtained from the method of fabricating may have one or more of a flexural modulus of about 0.2 GPa to about 100 GPa, a modulus of elasticity of about 0.2 GPa to about 100 GPa, or a tensile strength of about 1 MPa to about 1000 MPa as described herein in any embodiment.

In any embodiment herein, the method may further include sterilizing the biocompatible support structure. For example, in any embodiment herein, the sterilizing may include, but is not limited to, gamma irradiation, incubation with peracetic acid, autoclaving, UV irradiation, peroxide sterilization, supercritical fluid treatment, and the like or combinations thereof.

The fabricating of the tissue-engineered construct includes depositing one or more layers of one or more bio ink compositions as described herein in any embodiment. In any embodiment herein, the fabricating the tissue-engineered construct may include one or more fabrication systems or methods; for example, in any embodiment herein, the one or more fabrication systems or methods may include injection molding, rotational molding, positive molds, negative molds, subtractive manufacturing, milling and machining, and 3D printing. In any embodiment herein, the method of fabricating may include 3D printing as described herein in any embodiment. For example, in any embodiment herein, the depositing may include depositing one or more layers of the one or more bio ink compositions in or around the biocompatible support structure using a 3D printer; crosslinking the one or more bio ink compositions, and optionally repeating the depositing and crosslinking steps, to obtain the tissue-engineered construct; and curing the tissue or organ replacement composition.

Figure 4D:
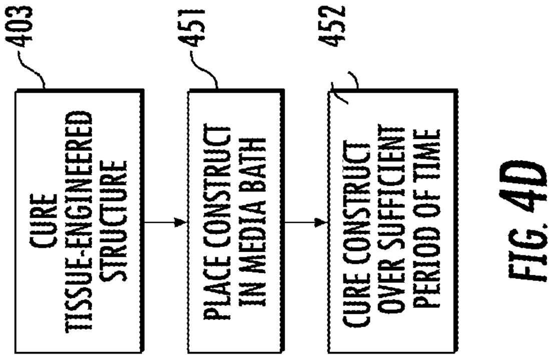
Figure 4C:
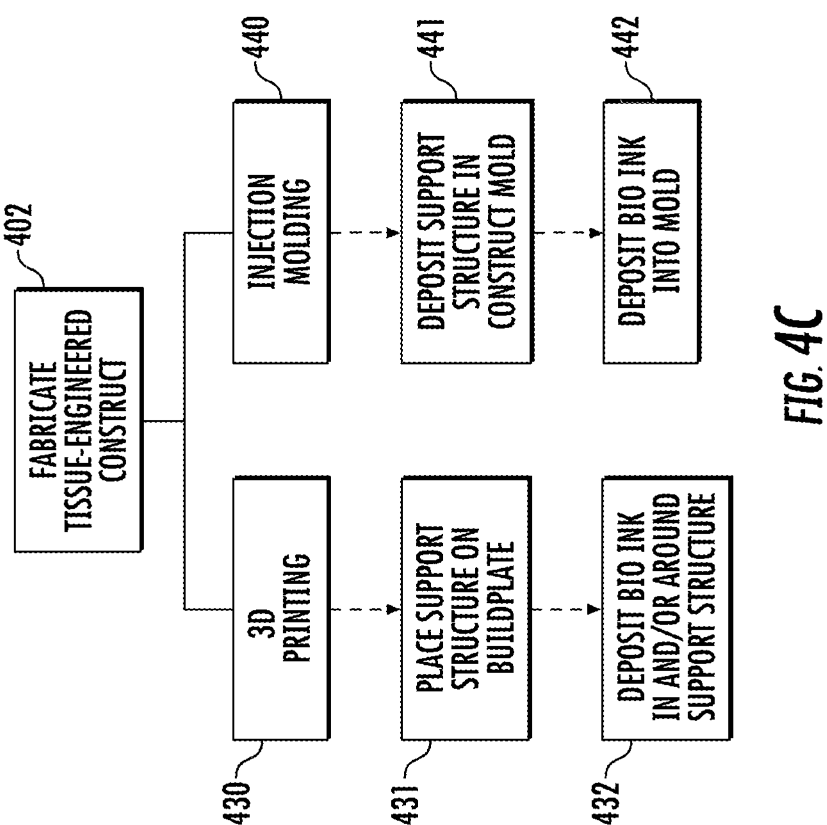

FIG. 4C depict a process 402 for fabricating a tissue-engineered construct according to at least one embodiment. The process 402 may include utilizing at least one 3D printer to print a biocompatible support structure (step 430). The process further includes placing the biocompatible support structure on a substrate (e.g., buildplate) (step 431) and depositing the bio ink in and/or around the biocompatible support structure (step 432).

Figure 3A:
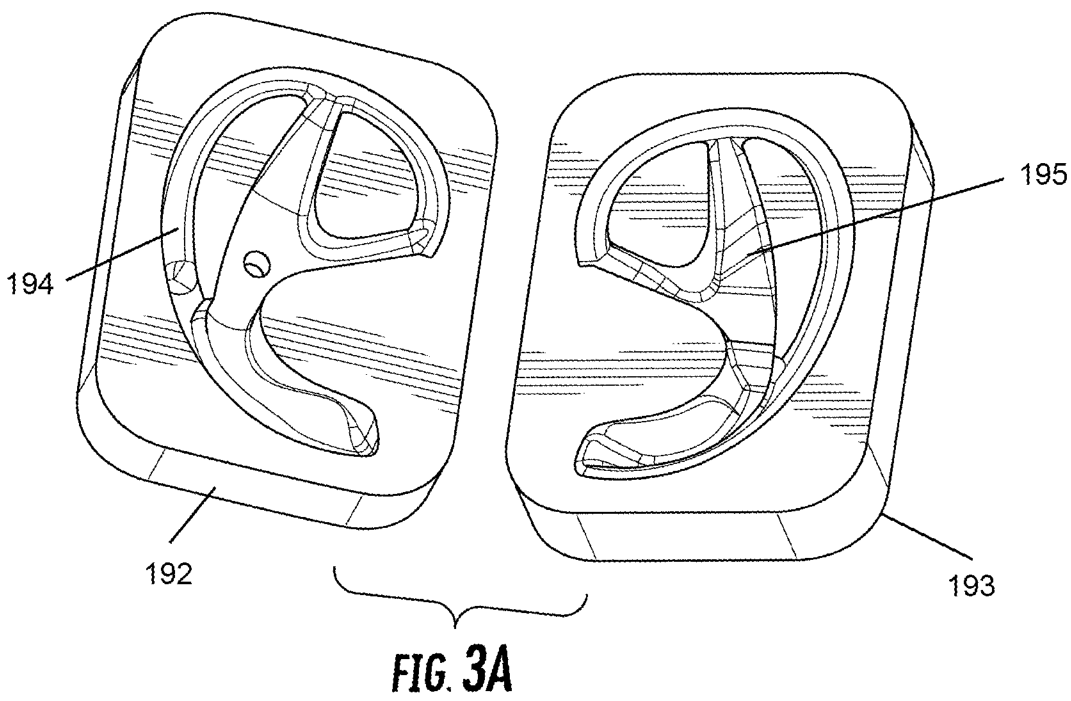
FIG. 3A shows an interior view of a mold configured and contoured for injection molding an ear shaped tissue-engineered construct according to an embodiment of the present technology.
Figure 3B:
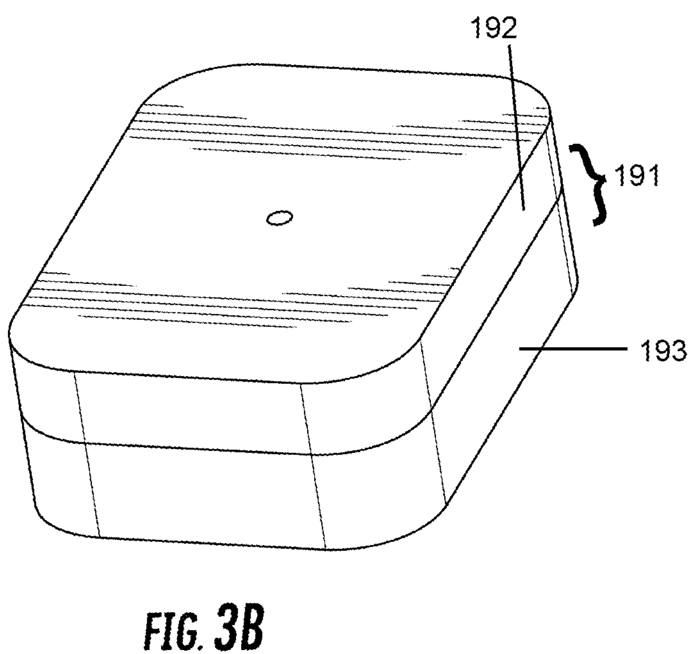
FIG. 3B shows an exterior view of a mold configured and contoured for injection molding an ear shaped tissue-engineered construct according to an embodiment of the present technology.

In any embodiment herein, fabricating the tissue-engineered construct may include injection molding. For example, in any embodiment herein, the depositing may include depositing the one or more bio ink compositions in a mold containing the biocompatible support structure; crosslinking the one or more bio ink compositions in the mold, and optionally repeating the depositing and crosslinking steps, to obtain the tissue-engineered construct; and curing the tissue or organ replacement composition, where the mold may be removed prior to or after the curing step. In any embodiment herein, the method may include removing the mold after curing the tissue or organ replacement composition. In any embodiment herein, the method may include removing the mold before curing the tissue or organ replacement composition. FIG. 3A shows an interior view of a mold 191 configured and contoured for injection molding an ear shaped tissue-engineered construct and having halves 191, 192 as first and second mold portions. Mold portion 192 includes a first cavity 194 and mold portion 193 includes a second cavity 195. FIG. 3B shows an exterior view of the mold 191 configured and contoured for injection molding an ear shaped tissue-engineered construct.

As discussed above, FIG. 4C depicts a process 402 for fabricating a tissue-engineered construct according to at least one embodiment. In certain embodiments, the process 402 includes fabricating the tissue-engineered construct via injection molding (step 440). The process may further include placing the biocompatible support structure in a mold (step 441) and depositing the bio ink into the mold (step 442).

In any embodiment herein, the bio ink is crosslinked. For example, in any embodiment herein, the bio ink may be subjected to crosslinking conditions to produce a crosslinked or polymerized bio ink. For example, in any embodiment herein, the crosslinking may include UV irradiation, addition of salts, neutralization of pH, thermal crosslinking, and the like or combinations thereof.

The tissue or organ replacement composition undergoes a curing step following crosslinking. In any embodiment herein, the method includes curing the tissue or organ replacement composition at a temperature of about 4° C. to about 50° C. Suitable curing temperatures may include, but are not limited to, about 4° C. to about 50° C., about 15° C. to about 45° C., about 30° C. to about 40° C., about 34° C. to about 37° C., about 35° C. to about 37° C., about 36° C. to about 37° C., and any range including and/or in between any two of the preceding values. In any embodiment herein, the tissue or organ replacement composition may be placed in a buffer solution or cell medium during the curing step. In any embodiment herein, suitable buffer solutions include, but are not limited to, phosphate buffered saline, sodium chloride solution, phosphate containing solutions, phosphate buffer solution, Hanks balanced salt solution, and IVIES buffer. Suitable cell medium may include, but is not limited to, serum, serum-free medium, HEPES, DMEM, and the like of combinations thereof, supplemented with bFGF, FBS, Ascorbate, and the like or combinations thereof. In any embodiment herein, the method may include curing the tissue or organ replacement composition in buffer solution and cell medium. In any embodiment herein, the curing may occur over a period of about 3 h to about 24 h. For example, in any embodiment herein, the curing period may be from about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h, or any range including and/or in between any two of the preceding values.

FIG. 4D provides a flow chart for a process in accordance with an embodiment. In particular, a process 403 of curing the tissue-engineered construct is shown. In accordance with an embodiment, process 403 includes placing the construct in a media bath (step 451) and allowing the construct to cure over a sufficient period of time (step 452).

In any embodiment herein, the one or more bio ink compositions may include, but are not limited to, alginate, agarose, collagen, chitosan, fibrin, hyaluronic acid, laminin, elastin, carrageenan, polyethylene oxide, polypropylene oxide, polyethylene oxide-co-polypropylene oxide, hydroxypropyl methyl cellulose, poly(propylene fumarate-co-ethylene glycol), poly(ethylene glycol)-co-poly(lactic acid), poly(vinyl alcohol), KDLl 2 oligopeptides, poly(n-isopropyl acrylamide), or combinations of two or more thereof. The one or more bio ink compositions may have a controlled rate of crosslinking through the adjustment of environmental variables including, but not limited to, temperature, pH, ionic strength, heat, light, or the addition of chemical crosslinking agents such as calcium, magnesium, barium, chondroitin, sulfate, and thrombin, riboflavin, carbodiimides, and the like. Suitable hydrogels for use in bio inks for tissue-engineered constructs are described in U.S. Pat. No. 9,044,335 entitled "COMPOSITE TISSUE-ENGINEERED INTERVERTEBRAL DISC WITH SELF-ASSEMBLED ANNULAR ALIGNMENT," filed on May 5, 2010, the entire contents of which are hereby incorporated by reference.

In any embodiment herein, the one or more bio ink compositions may include alginate hydrogel as described herein in any embodiment. For example, in any embodiment herein, the alginate hydrogel may be present in an amount from about 0.5% (w/v) to about 10% (w/v). In any embodiment herein, the one or more bio ink compositions may include collagen as described herein in any embodiment. For example, in any embodiment herein, the one or more bio ink compositions may include collagen in an amount greater than about 5 mg/ml. In any embodiment herein, the one or more bio ink compositions may include type I collagen, type II collagen, or a combination thereof.

In any embodiment herein, the one or more bio ink compositions may further include a neutralizer and cellular media as described herein in any embodiment. Suitable neutralizers may include, but are not limited to, formulations containing weak acid, for instance. In any embodiment herein, the one or more bio ink compositions may be cellular or acellular. For example, in any embodiment herein, the one or more bio ink compositions may include cellular media containing living cells. The cellular media may further include other living cells; for example, in any embodiment herein, the bio ink may include epidermal cells, chondrocytes and other cells that form mesenchymal stem cells, adipose derived stem cells, macrophages, adipocytes, dermal cells, muscle cells, hair follicles, fibroblasts, organ cells, osteoblasts, osteocytes and other cells that form bone, endothelial cells, mucosal cells, pleural cells, ear canal cells, tympanic membrane cells, peritoneal cells, Schwann cells, corneal epithelial cells, gingiva cells, central nervous system neural stem cells, tracheal epithelial cells, or combinations of two or more thereof. In any embodiment herein, the one or more bio ink compositions may be acellular, where the one or more bio ink compositions do not contain living cells.

In any embodiment herein, the one or more bio ink compositions may further include carriers or additives. Suitable carriers may include, but are not limited to, water, aqueous ionic salt solutions (e.g., sodium hydroxide), phosphate buffer saline (PBS), cell medium, fetal bovine serum (FBS), Dulbecco's minimum essential medium (DMEM), fibroblast growth factor (bFGF), or the like or combinations thereof. Suitable additives include, but are not limited to, crosslinking agents. Suitable crosslinking agents include, but are not limited to, riboflavin, ribose, polyethylene glycol (PEG), glutaraldehyde, 1-ethyl-3-(3-dimethylaminopropyl)-carbodiimide hydrochloride, genipin, chitosan, or the like or combinations thereof.

In any embodiment herein, the fabricating the biocompatible support structure or fabricating the tissue-engineered construct may occur sequentially or concurrently.

In any embodiment of the method, the tissue-engineered construct may be configured to have any suitable shape or size. For example, in any embodiment herein, the tissue-engineered construct may have a customized 3D structure of various shapes and sizes for a number of clinical applications, such as facial or craniofacial applications, engineered cartilage tissue, or combinations thereof. In any embodiment herein, the tissue-engineered construct may have a shape of an organ or tissue of a subject. For example, in any embodiment herein the organ or tissue is selected from an ear, a nose, meniscus, articular cartilage, trachea, or a heart valve. In any embodiment herein, the organ is an ear.

In any embodiment herein, the tissue-engineered construct may have a 3D structure based on a 3D computer model. For example, in any embodiment herein, the computer based model may include a 3D contralateral organ or tissue of a subject. In any embodiment herein, the subject is a mammal (e.g., a cat, dog, rodent, or primate). In any embodiment herein, the subject is a human. The computer based 3D model may be obtained via 3D imaging tools. Suitable 3D imaging tools include, but are not limited to, clinical computed tomography (CT), magnetic resonance imaging (MM), laser scanning, 3D cameras, or combinations of any two or more thereof.

In any embodiment herein, the tissue or organ replacement composition may withstand one or more of a compression of about 1 kN to about 10,000 kN or a shear force of about 0.2 kN to about 1,000 kN as described herein in any embodiment.

In at least one embodiment, the methods of fabricating a tissue or organ replacement composition of the present technology is a method according to the steps illustrated in FIGS. 4A-4D.

The present invention, thus generally described, will be understood more readily by reference to the foregoing examples, which are provided by way of illustration and are not intended to be limiting of the present invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

While this specification contains many specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The terms "coupled," "connected," and the like as may be used herein mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another or with the two components or the two components and any additional intermediate components being attached to one another.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A method of making a tissue or organ replacement composition to be attached to or implanted in a patient, the method comprising:

fabricating a biocompatible support structure including one or more external supports, one or more internal supports, or combinations thereof of a biocompatible material;

fabricating a tissue-engineered construct including one or more bio ink compositions, fabricating the tissue engineered construct comprising:

depositing the one or more bio ink compositions in or around the biocompatible support structure, wherein the one or more bio ink compositions includes living cells;

crosslinking the one or more bio ink compositions, and optionally repeating the depositing and crosslinking steps, to form the tissue-engineered construct; and curing the tissue or organ replacement composition;

wherein:

the tissue or organ replacement composition has a 3D shape;

the biocompatible material is present in an amount of about 1% to about 100% by weight of the biocompatible support structure;

wherein the one or more external supports partially cover outer surfaces of the tissue-engineered construct when the tissue or organ replacement composition is configured to be attached to or implanted in the patient and/or the one or more internal supports are partially encapsulated by the tissue-engineered construct when the tissue or organ replacement composition is configured to be attached to or implanted in the patient; and wherein the organ is an ear and/or the biocompatible support structure is configured to be both internal and external to the body of the patient when attached to or implanted in the patient.

2. The method of claim 1, wherein the method of fabricating the biocompatible support structure comprises:

depositing one or more layers of the biocompatible material to a substrate; crosslinking the biocompatible material; and separating the substrate from the one or more external supports, the one or more internal supports, or the combination thereof.

3. The method of claim 2, wherein the depositing comprises 3D printing the one or more bio ink compositions.

4. The method of claim 3, wherein the 3D printing is selected from the group consisting of ink-jet printing, layer-by-layer printing, extrusion printing, and bioprinting.

5. The method of claim 2, further comprising repeating the depositing and crosslinking steps to obtain the one or more external supports, the one or more internal supports, or the combination thereof.

6. The method of claim 1, wherein the method of fabricating the biocompatible support structure comprises injection molding, wherein the injection molding comprises:

depositing one or more layers of the biocompatible material to a substrate, wherein the substrate is a mold of the one or more external supports, internal supports, or combinations thereof;

crosslinking the biocompatible material in the mold; and removing the one or more external supports, internal supports, or the combination thereof from the mold.

7. The method of claim 1, wherein the method of fabricating the biocompatible support structure comprises thermoforming, wherein the thermoforming comprises:

contacting a 2D sheet of the biocompatible material to a substrate, wherein the substrate is a mold of the one or more external supports, internal supports, or the combination thereof;

heating the 2D sheet of the biocompatible material to thermoform the 2D sheet into conformity with the shape of the mold to obtain the one or more external supports, internal supports, or the combination thereof;

removing the one or more external supports, internal supports, or the combination thereof from the mold.

8. A tissue or organ replacement composition to be attached to or implanted in a patient, the tissue or organ replacement composition comprising:

a tissue-engineered construct comprising one or more bio ink compositions; and a biocompatible support structure comprising one or more external supports, one or more internal supports, or combinations thereof of a biocompatible material;

wherein the tissue or organ replacement composition has a three-dimensional (3D) shape;

wherein the biocompatible material is present in an amount of 1% to 100% by weight of the biocompatible support structure;

wherein the one or more external supports partially cover outer surfaces of the tissue-engineered construct when the tissue or organ replacement composition is configured to be attached to or implanted in the patient and/or the one or more internal supports are partially encapsulated by the tissue-engineered construct when the tissue or organ replacement composition is configured to be attached to or implanted in the patient; and wherein the organ is an ear and/or the biocompatible support structure is configured to be both internal and external to the body of the patient when attached to or implanted in the patient.

9. The composition of claim 8, wherein the one or more bio ink compositions comprise one or more of hydrogel, agarose, collagen, laminin, elastin, chitosan, fibrin, hyaluronic acid, carrageenan, polyethylene oxide, polypropylene oxide, polyethylene oxide-co-polypropylene oxide, hydroxypropyl methyl cellulose, poly(propylene fumarate-co-ethylene glycol), poly(ethylene glycol)-co-poly(lactic acid), poly(vinyl alcohol), KDLI 2 oligopeptides, poly(n-isopropyl acrylamide), or combinations of two or more thereof.

10. The composition of claim 9, wherein the one or more bio ink compositions comprise an alginate hydrogel present in an amount of 0.5% (w/v) to 10% (w/v).

11. The composition of claim 8, wherein the one or more bio ink compositions comprise 5 mg/ml to 200 mg/ml of collagen and/or comprise a carrier, a crosslinking agent, or a combination thereof.

12. The composition of claim 8, wherein the one or more bio ink compositions comprise collagen selected from type I collagen, type III collagen, type IV collagen, other fibrillary collagens, or a combination of two or more thereof.

13. The composition of claim 8, wherein the biocompatible material is selected from the group consisting of polysaccharides, biocompatible polymers, rubber, silicon, biocompatible metals, biocompatible ceramics, polyethylene glycol, polypropylene glycol, polyamino acids, natural and biopolymers, and combinations of two or more thereof and/or wherein the biocompatible material is selected from the group consisting of poly(lactic acid) (PLA), poly(glycolic acid) (PGA), poly (lactic-co-glycolic acid) (PLGA), polydioxanone (PDO), polycaprolactones, bioresorbable metal alloys, and combinations thereof.

14. The composition of claim 8, wherein the one or more internal supports have a 2D thickness from 10 μm to 2000 μm.

15. The composition of claim 8, wherein the biocompatible support structure has one or more of a flexural modulus of 0.2 GPa to 100 GPa, a modulus of elasticity of 0.02 GPa to 100 GPa, or a tensile strength of 1 MPa to 1000 MPa.

16. The composition of claim 8, wherein the composition withstands compression of 1 kN to 10,000 kN, a shear force of 0.2 kN to 1,000 kN, or a combination thereof.

17. The composition of claim 8, wherein the bio ink composition includes a cellular media containing a population of cells;

wherein the cellular media is a cellular hydrogel, and wherein the one or more bio ink compositions further comprise collagen.

* * * * *